United States Patent
Sadoff et al.

(10) Patent No.: US 6,315,999 B1
(45) Date of Patent: Nov. 13, 2001

(54) PHARMACEUTICAL PRODUCT FOR THE TREATMENT OF SEPSIS

(75) Inventors: Jerald C. Sadoff, Washington, DC (US); Steven Michael Opal, Pawtucket, RI (US); Alan S. Cross, Washington, DC (US); Mark William Bodmer, Oxfordshire (GB)

(73) Assignee: Solvay, S.A., Brussels (BE)

( * ) Notice: Subject to any disclaimer, the term of this patent is extended or adjusted under 35 U.S.C. 154(b) by 0 days.

(21) Appl. No.: 08/253,217

(22) Filed: Jun. 2, 1994

Related U.S. Application Data

(62) Continuation of application No. 08/008,874, filed on Jan. 25, 1993, now abandoned, which is a continuation of application No. 07/849,031, filed as application No. PCT/US90/04434 on Aug. 10, 1990, now abandoned.

(30) Foreign Application Priority Data

Aug. 10, 1989 (GB) .................................................. 8918232

(51) Int. Cl.[7] .................. A61K 39/395; A61K 39/40; C07K 14/00
(52) U.S. Cl. .................... 424/145.1; 424/158.1; 424/164.1; 424/169.1; 530/351
(58) Field of Search .......................... 530/351; 424/95.1, 424/145.1, 150.1, 164.1, 169.1; 435/158.1

(56) References Cited

FOREIGN PATENT DOCUMENTS

| | | |
|---|---|---|
| 355067 | 2/1990 | (EP) . |
| 374510 | 6/1990 | (EP) . |
| 2186592 | 8/1987 | (GB) . |

OTHER PUBLICATIONS

Opal et al., "Monoclonal Antibody Directed Against Tumor Necrosis Factor Protects Neutropenic Rats from Lethal Pseudomonas Sepsis," *1989 ASM Annual Meeting*, Official Abstract, May 14–18, 1989.
Opal et al. 1990 J. Infect. Disease 161: 1148–1152.*
Beutler et al 1985 Science 229:869.*
Ziegler et al 1982 New Eng J Med. 307:1225.*
WO 90/00902, Kuo, Monoclonal Antibodies Reactive with Cachectin, Feb. 1990, See pp. 2, 3, 9 and 10.
Collins et al: "Oral Ciprofloxacin and a Monclonal Antibody to Lipopolysaccharide Protect Leukopenic Rats from Lethal Infection with *Pseudomonas aeruginosa*" The Journal of Infectious Diseases, vol. 159, No. 6, Jun. 1989.
Mathison et al: "Participation of Tumor Necorsis Factor in the Mediation of Gram Negative Bactrial Lipopoly–saccha–ride–induced injury in Rabbits" J.ClinInvest, vol. 81, No. 6, Jun. 1988.

* cited by examiner

*Primary Examiner*—Karen Cochrane Carlson
(74) *Attorney, Agent, or Firm*—Venable; Marina V. Schneller

(57) ABSTRACT

An antibody to tumor necrosis factor-α (anti-TNF) and an antibody to bacterial lipopolysaccharide (anti-LPS) used together in a neutropenic rat model of sepsis are shown to enhance survival of the rats relative to either antibody used alone. Pharmaceutical products including each of the components are therefore of utility in therapy of sepsis. The anti-LPS antibody included may be specific for the O-specific clain of a particular bacterial lipopolysaccharide (serotype specific antibody) but preferably recognizes the core glycolipid of lipopolysaccharide.

13 Claims, 3 Drawing Sheets

PHARMACEUTICAL PRODUCT FOR THE TREATMENT OF SEPSIS

This application is a continuation application Ser. No. 08/008,874, filed Jan. 25, 1993, now abandoned, which is a continuation of Ser. No. 07/849,031, filed Apr. 9, 1992, now abandoned, which is a national stage application of PCT/US90/04434, filed Aug. 10, 1990, which calims foreign priority to GB 8918232.3, filed Aug. 10, 1989.

TECHNICAL FIELD

The present invention relates to pharmaceutical products for the treatment of sepsis and, in particular to products including an antibody to TNF-α (tumour necrosis factor alpha). As used herein the term sepsis encompasses Gram negative and Gram positive bacteremia, septicemia and endotoxemia, as well as septic (or endotoxic) shock.

BACKGROUND ART

Septic shock is a condition which may be associated with Gram positive infections, such as those due to pneumococci and streptococci, or with Gram negative infections, such as those due to *Escherichia coli*, Klebsiella-Enterobacter, Pseudomonas, and Serratia. In the case of the Gram-negative organisms the shock syndrome is not due to bloodstream invasion with bacteria per se but is related to release of endotoxin, the lipopolysaccharide (LPS) moiety of the organisims' cell walls, into the circulation.

Septic shock is characterized by inadequate tissue perfusion and circulatory insufficiency due to diffuse cell and tissue injury and the pooling of blood in the microcirculation. Hypotension, oliguria, tachycardia, tachypnea and fever are observed in most patients.

The mortality rate associated with septic shock from gram negative bacteremia remains unacceptably high despite the availability of a wide variety of potent antimicrobial agents. The failure of antimicrobial agents to improve the outlook in septic shock is related to large part to the intrinsic toxicity of endotoxin (LPS) produced by gram negative bacteria. Antibiotics have no immediate effect on endotoxin and may transiently elevate circulating endotoxin levels following the initiation of therapy during Gram negative bacteremia.

Alternative measures have been sought to prevent the deleterious effects of endotoxemia. An attractive strategy has been the development of active or passive immunotherapy against endotoxin itself. Serotype specific immunity to LPS and polyclonal and monoclonal antibody immunotherapy directed against the core glycolipid of gram negative bacterial LPS have been at least partially successful in a number of experimental and clinical studies of septic shock.

Recent evidence indicated that the monocyte/macrophage derived cytokine, tumour necrosis factor-alpha, is a principal mediator of the hemodynamic and pathophysiologic effects of endotoxin. Polyclonal and monoclonal antibodies directed against tumor necrosis factor have demonstrated protective efficacy against potentially lethal doses of endotoxin as well as large intravenous doses of *Escherichia coli*.

DISCLOSURE OF THE INVENTION

The present inventors have now established that by using a combination of antibody to the cytokine TNF-α and antibody to LPS for the treatment of septic shock significant additional decreases in mortality relative to either antibody used alone, may be produced.

Thus, according to the present invention there is provided a pharmaceutical product containing an antibody to endotoxin (hereinafter referred to as anti-LPS) and an antibody to TNF-α (hereinafter referred to as an anti-TNF) as a combined preparation for simultaneous mixed, simultaneous separate, or sequential, use in therapy of sepsis.

In one embodiment of the invention the pharmaceutical product may take the form of a pharmaceutical composition comprising anti-LPS and an anti-TNF and, optionally, a pharmaceutically acceptable, excipient diluent or carrier. The pharmaceutical composition is suitably for use in therapy of sepsis.

A further aspect of the invention provides for the use of an anti-LPS and an anti-TNF, in the manufacture of a pharmaceutical product for the treatment of sepsis. The invention also provides for the treatment of sepsis in animals, and in particular in man, by the combined administration of an anti-TNF and an anti-LPS. The pharmaceutical product of the present invention is particularly suitable for the treatment of septic shock associated with Gram negative endotoxemia. In addition, it is particularly suitable for the treatment of patients who are neutropenic for example because they are receiving chemotherapy for cancer.

The anti-TNF and anti-LPS antibodies for use according to the present invention may in general belong to any immunoglobulin class. Thus, for example anti-TNF or anti-LPS antibodies of immunoglobulin class G and/or immunoglobulin class M may be employed.

Each antibody may be of animal, for example mammalian origin and may be for example of murine, rat or human origin. Each may be a whole immunoglobulin, or a fragment thereof, for example a F(ab')$_2$, Fab' or Fab fragment, or a fragment obtained by recombinant DNA techniques, for example Fv fragments (as described in International Patent Application WO89/02465).

The anti-TNF antibody may be polyspecific but is preferably monospecific and, particularly preferably is monospecific for human TNF-α. The anti-LPS antibody may, likewise, be polyspecific or monospecific for LPS. The LPS molecule consists of a heteropolysaccharide chain covalently linked to a glycolipid (lipid A or core glycolipid). Part of the heteropolysaccharide chain, known as the core polysaccharide, has a structure which appears to be similar, or identical in closely-related strains of bacteria. The remainder of the chain is called the O-specific chain and is highly variable in composition. The anti-LPS antibody may be monospecific for the O-specific chain but is preferably monospecific for the core polysaccharide and particularly preferably for the core glycolipid. For example, it may be specific for the core glycolipid of LPS from the J5 mutant of *E. coli*.

The antibodies may be polyclonal or monoclonal antibodies but are preferably monoclonal. Particularly useful antibodies for use according to the invention include recombinant anti-TNF and anti-LPS antibodies i.e. antibodies which have been produced using recombinant DNA techniques.

Especially useful recombinant antibodies include, (1) those having an antigen binding site at least part of which is derived from a different antibody, for example those in which the hypervariable or complementarity determining regions of one antibody have been grafted into the variable framework regions of a second, different, and preferably human, antibody (as described in European Patent Application EP-A-239400); (2) recombinant antibodies or fragments wherein non-Fv sequences have been substituted by non-Fv sequences from other, different antibodies (as described in European Patent Application EP-A-171496, EP-A-173494 and EP-A-194276); and (3) recombinant antibodies or fragments possessing substantially the structure of a natural immunoglobulin but wherein the hinge region has a different number of cysteine residues from that found in the natural immunoglobulin, or wherein one or more cysteine residues in a surface pocket of the recombinant antibody or fragment is in the place of another amino acid residue present in the natural immunoglobulin (as described in International Patent Application Nos. WO89/01974 and WO89/01782 respectively).

Each antibody (anti-TNF, anti-LPS) may be prepared using well-known immunological techniques employing the TNF-α or LPS as antigen. Thus, in the case of anti-TNF for example, any suitable host may be injected with TNF-α and the serum collected to yield the desired polyclonal anti-TNF antibody after appropriate purification and/or concentration, (for example by affinity medium). Alternatively, splenocytes or lymphocytes may be recovered from the TNF injected host and immortalised using for example the method of Kohler et al. Eur. J. Immunol. 6, 511, (1976), the resulting cells being diluted and cloned to obtain a single genetic line producing monoclonal anti-TNFα antibodies in accordance with conventional practice. Antibody fragments may be produced using conventional techniques for example by enzymatic digestion e.g. with pepsin [Parham, J. Immunol. 131, 1985, (1983)] or papain [Lamoyi and Nisonoff, J. Immunol. 56, 235, (1983)]. Where it is desired to produce recombinant anti-TNFα antibodies, these may be produced using for example the methods described in European Patent Specifications Nos. 171496, 173494, 194276 and 239400.

Corresponding techniques can be employed for the production of anti-LPS antibodies.

The pharmaceutical product and composition of the invention may take any suitable form for administration and in particular will be in a form suitable for parenteral administration, for example by injection or infusion, e.g. by bolus injection or continuous infusion. Compositions for injection may take the form of suspensions, solutions or emulsions of either or both antibodies in oily or aqueous vehicles and may contain conventional formulatory agents such as suspending, stablising and/or dispersing agents. Alternatively, the product and composition may be in a dry form, for reconstitution before use with an appropriate sterile liquid. The pharmaceutical product and composition of the present invention may contain one or more additional active ingredients. For example, each may include an anti-microbial agent, such as a penicillin, cephalosporin, carbaphem, tetracycline, or amyloglycoside, chloramphenicol, erythromycin, vancomycin, amphoterocin or ciprofloxacin.

The pharmaceutical product and composition of the present invention may be used prophylactically, or in the treatment of an existing condition. The dose at which the anti-TNF and anti-LPS antibodies will be administered to a patient will depend on the nature and severity of his condition, and on whether the antibody is being used prophylactically or to treat an existing condition and may be determined by the skilled physician. The anti-TNF antibody may, for example, be administered by infusion at a dose in the range 0.1 to 20 mg/kg, one to four times a day. Suitable doses of anti-LPS might be in the range of 0.1 to 2.5 mg/kg one to four times a day.

BRIEF DESCRIPTION OF THE DRAWINGS

Embodiments of the invention are now illustrated by way of example only and with reference to the accompanying drawings of which.

Figure 3:
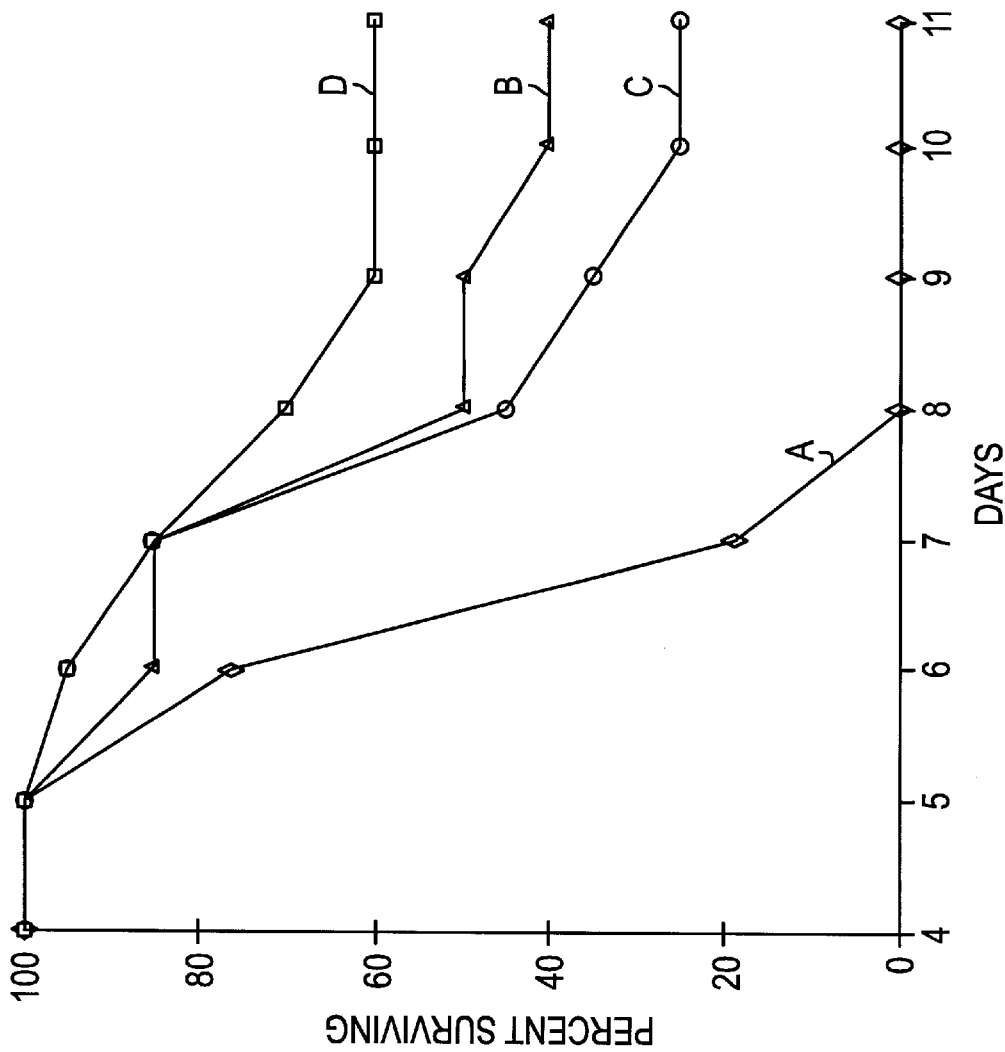

—●— (control) 3 ml/kg preimmune rabbit serum;
—○— Anti-J5 serum (3 ml/kg); —▲— Anti-J5 (1.5 ml/kg); —□— Anti-J5 (0.75 ml/kg); —✳— Anti-J5 (0.375 ml/kg);

FIG. 3 shows percent survival against time of *Pseudomonas aeruginosa* challenged neutropenic rats who received treatment with preimmune rabbit serum (Curve A), monoclonal anti-TNF (20 mg/kg) (Curve B), polyclonal anti-J5 serum (1.5 ml/kg) (Curve C), or both monoclonal anti-TNF and polyclonal anti-J5 (Curve D).

MODES FOR CARRYING OUT THE INVENTION

In the examples which follow a neutropenic rat model of Pseudomonas sepsis is employed to determine whether the combination of an anti-TNF monoclonal antibody with an anti-LPS monoclonal antibody would be of additional benefit relative to either antibody used separately in preventing Pseudomonal sepsis in this animal model. The model is of interest since patients who are undergoing chemotherapy for conditions are neutropenic and therefore particularly susceptible to sepsis. The neutropenic rat model of pseudomonas sepsis is described in detail in Journal of Infectious Diseases (1990), 161: 1148–1152.

EXAMPLE 1

Methods
A. Animal Model—Pathogen free nonpregnant, female Sprague-Dawley rats weighing between 125–175 grams were rendered neutropenic by the IP administration of cyclophosphamide at 150 mg/kg at time 0 followed by a second dose of 50 mg/kg 72 hours later.

This dose of cyclophosphamide was found to reproducibly result in profound neutropenia within 3–5 days after the first dose and lasting 5–7 days in these animals. In the absence of an infectious challenge this dose of cyclophosphamide was not lethal to the experimental animals. Following premedication with intramuscular cefamandole (100 mg/kg given intramuscularly every other day) to inhibit aerobic intestinal microflora, a challenge of a virulent human strain of *Pseudomonas aeruginosa* 12.4.4 (provided by Dr A. McManus, San Antonio, Tex.) was given by orogastric feeding tube at 0, 48 and 96 hours after the first dose of cyclophosphamide. The challenge was given at a dose of approximately $10^6$ organism in 1 ml PBS.

All manipulations of the animals were conducted under light $CO_2$ anaesthesia to minimize trauma to the animals.

Twenty-four hours prior to cyclophosphamide and again at 72 and 120 hours after cyclophosphamide, quantitative blood cultures, complete blood counts and serum specimens were obtained from all animals. Animals were examined daily and any deaths recorded with necropsy examinations performed within 24 hours after death.

B. Monoclonal antibody treatment

1. A hamster derived anti-murine TNF-alpha monoclonal antibody (TN3 19.12—from Schreiber, Washington University, St. Louis, Mo. and provided by Celltech Ltd., Slough, UK) was utilised in this animal model. Previous experiments have demonstrated that this monoclonal antibody neutralised natural rat tumor necrosis factor in cytotoxicity assays. The monoclonal antibody was given intravenously at time 0 and 120 hours at a dose of 20 mg/kg via the tail vein. Previous experiments indicated that this was optimal protective dose in this animal model.

2. A serotype specific monoclonal antibody directed against O-specific side chain LPS of Pseudomonas aeruginosa 12.4.4 (designated MAb 11.14.1) was obtained from mouse ascitic fluid as previously described (Collins, H. H., et al J. Infect, Dis. 159: 1073–1082), using the lipopolysaccharide of P. aeruginosa 12.4.4 which belongs to Fisher-Devlin Gnabasik immunotype 6 in pristane-primed BALB/c mice. This monoclonal antibody is of the IgG isotype and was given intravenously at a dose of 2.5 mg/kg at time 0 and 120 hours. This dose was chosen since previous experiments using intraperitoneal injections offered partial protection when administered every 48 hours to neutropenic rats.

3. As a control, an irrelevant monoclonal antibody-L2 3DP (a hamster derived monoclonal antibody directed against recombinant murine IL2 which does not react to natural mouse or rat IL2) was given to sixteen control animals at the same dosing intervals as the other monoclonal antibody preparations to determine if an irrelevant monoclonal antibody given at the same concentration would have any salutary effect on neutropenic animals in this experimental model. As a further control an equal volume of normal saline was given to a further group of rats, again at the same dosing interval as the monoclonal antibody preparations.

C. Measurements

1. Serum TNF levels were measured using the L929 fibroblast cytotoxicity assay 24 hours prior to the first dose of cyclophosphamide and 120 hours later. Serum levels of anti-TNF monoclonal antibody levels 4 hours after an intravenous administration of 20 mg/kg TN3 19.12 were determined in a direct ELISA using a peroxidase labelled goat anti-hamster IgG antibody. Serum levels of the anti-LPS monoclonal antibody 11.14.1 were measured with an ELISA system with outer membrane complex as the antigen as previously described (Collins H. H. et al., Supra).

Blood cultures and complete blood counts were performed 24 hours prior to cyclophosphamide and at 72 and 120 hours. Necropsy examination included cultures of lung, heart, spleen, liver, and cecum. Histologic sections were obtained in five lethally infection control animals of cecum, liver, lung and renal tissue. Statistical analysis was performed using analysis of variance or two tailed student's T-test where appropriate.

Results

Figure 1:
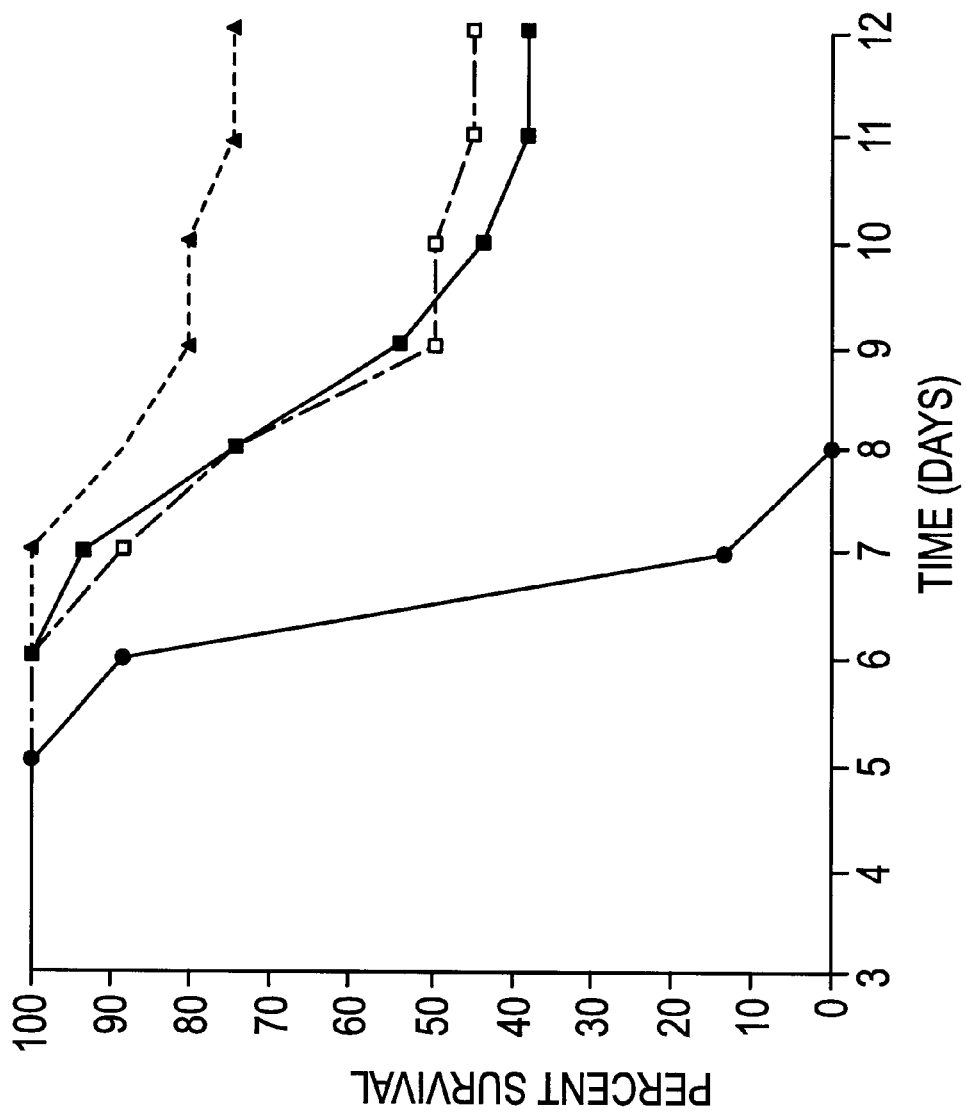
FIG. 1 shows percent survival of neutropenic rats against time. Rats in each test group were given the following treatments; Group 1 (●——●)—Pseudomonas challenge accompanied by treatment with an irrelevant monoclonal antibody; Group 2 (□——□)—Pseudomonas challenge accompanied by treatment with anti-TNF monoclonal antibody; Group 3 (■——■)—Pseudomonas challenge accompanied by treatment with monoclonal anti-LPS against *Pseudomonas aeruginosa* 1244; Group 4 (▲- - -▲)—Pseudomonas challenge accompanied by treatment with both anti-TNF and anti-LPS antibodies.

The results of the experiment are illustrated in FIG. 1.

L2 3D9 irrelevant monoclonal antibody treated control animals (Group 1) experienced a 100% mortality rate with 0/16 animals surviving the ten day study period. Animals which received saline alone (n=16) also had a 100% mortality rate (data not shown).

Animals treated with anti-TNF monoclonal antibody alone (Group 2) had a survival rate of 44% (7/16). Anti-TNF mAb provided a significant survival advantage over Group 1 from lethal Pseudomonas sepsis ($P<0.02$).

Group 3 animals received anti-LPS antibody with saline or irrelevant monoclonal antibody control and exhibited a 37% survival (6/16) which also is significantly better that the Group 1 animals ($P<0.05$).

Group 4 animals, which received anti-LPS as well as anti-TNF monoclonal antibody had a 75% survival rate (12/16) which was significantly improved over either monoclonal antibody alone ($P<0.05$).

Anti-TNF monoclonal antibody serum levels measured 3–4 hours after intravenous administered of TN3 19.12 was 398±69 mog/ml while anti-LPS monoclonal antibody levels were measured at 508±41 ng/ml. All animals were found to be severely neutropenic with absolute granulocyte counts of <100 granulocytes/mm$^3$ by 120 hours. Random blood cultures obtained during the period of neutropenia revealed no difference in the frequency or magnitude of bacteremia with the infecting strain P. aeruginosa 1244. The frequency of bacteremia was 36% Group 1; 42% Group 2; 36% Group 3; and 38% Group 4. Serum TNF levels were undetectable prior to cyclophosphamide but were elevated at 120 hours to 402±217 pg/ml in control animals and 32±66 pg/ml in anti-TNF mAb treated animals ($p<0.00003$).

Necropsy examination of animals which did not survive the period of neutropenia revealed that 93% had evidence of multi-system infection with the infecting strain of P. aeruginosa 12.4.4. One animals died of apparent gastrointestinal hemorrhage and a second animal had pulmonary hemorrhage. Animals which survived the period of neutropenia (5–7 days) were sacrificed at the end of the experiment. Organ cultures were negative in all animals with the exception of cecal cultures which remained positive in 30%.

Histologic examination of lethally infected control animals revealed mild pulmonary congestion and interstitial edena in lung tissue and cecal specimens as well as evidence of acute tubular necrosis of renal tissue.

EXAMPLE 2

The data presented above in Example 1 indicate the potential utility of an anti-LPS and an anti-TNF antibody used together in the treatment of sepsis. The anti-LPS employed was directed against the O-specific side chain of the infecting microorganism and was therefore specific for the particular strain of microorganism employed. Since, in general, the serotype of the infecting strain is unknown at the time a patient develops septic shock it is desirable to administer a cross-protective anti-LPS antibody in order to give broad protection in a number of clinical infections.

The present inventors have therefore investigated the effect of a polyclonal antiserum directed to the core glycolipid of LPS when used in conjunction with the monoclonal anti-TNF, TN3 19.12.

Figure 2:
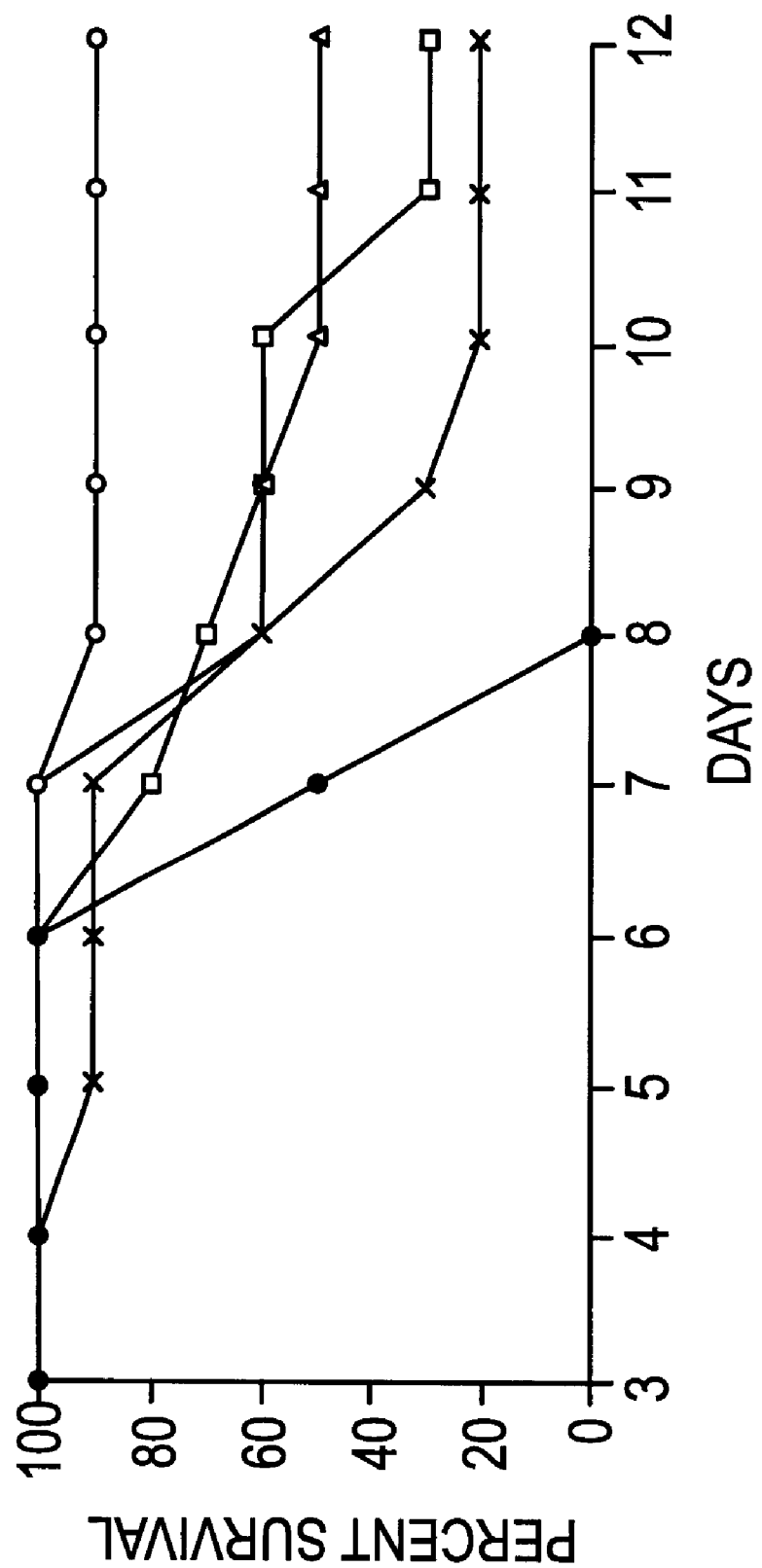
FIG. 2 shows percent survival against time of *Pseudomonas aeruginosa* challenge neutropenic rats which received various doses of a rabbit polyclonal antiserum against the core glycolipid of LPS of the J5 mutant of *E. coli*. Doses were as follows.

The polyclonal antiserum employed was a rabbit derived antiserum to E. coli J5; this is a standard polyclonal antiserum directed against the core glycolipid of gram negative bacteria (Warren, H. S. et al, Infection and Immunity, (1987), 55, 1668–1673). In a preliminary set of experiments the inventors determined the effect of this polyvalent antiserum on the prevention of lethality in the neutropenic rat model of Pseudomonas sepsis. Experiments were carried out as described above at Example 1, except that a single dose only of antiserum was administered intravenously at the onset of fever. Groups of ten rats received various doses of anti-J5 rabbit serum or of pre-immune rabbit serum; the results of these experiments are shown in FIG. 2 which indicates that the protective dose of antiserum necessary to produce 50% survival of the animals was around 1.5 ml/kg.

Having established this protective dose further experiments were carried out in which the effects of a single dose of anti-TNF monoclonal antibody (20 mg/kg TN3 19.12), of J5 antiserum (1.5 ml/kg), of a combination of both the J5 antiserum and the anti-TNF monoclonal antibody, or of a control consisting of pre-immune rabbit serum were compared. In each case the treatment was administered at the onset of fever (generally 4–6 days from the first cyclophosphamide administration). The incidence of documented bacteremia with the test strain *P. aeruginosa* 12.4.4 was 73.3% in this experiment.

The results are shown in FIG. 3 and demonstrate that 12 of 20 animals in the combination group (Trace D of FIG. 3) survived; 8 of 20 anti-TNF treated animals survived (Trace B of FIG. 3); 5 of 20 animals given J5 antisera survived (Trace C of FIG. 3); and 0 of 20 control animals given preimmune rabbit serum survived.

The results indicate that the combination of the J5 antiserum and anti-TNF is superior to the control (p<0.0001) in preventing mortality in this model of Pseudomonas sepsis. Furthermore, while the J5 antiserum alone (p=0.055) and the anti-TNF monoclonal antibody alone (p<0.01) offered some protection compared to the control, the combination of J5 antiserum and anti-TNF was significantly better than either given alone (p<0.05). The results therefore demonstrate that advantageous effects can be achieved by employing an antibody to TNF in conjunction with an antibody to the core glycolipid of LPS.

Conclusions

The results of these experiments indicate that anti-TNF monoclonal antibody alone, even in the absence of antimicrobial agents, will protect animals from otherwise lethal Pseudomonas infection during a period of chemotherapy induced neutropenia. Antibody directed against the LPS of the infecting strain also offers partial protection against the lethal effects of Pseudomonas sepsis in neutropenic rats as shown in Example 1. However the combination of anti-TNF and anti-LPS monoclonal antibody offered the best of protection in Example 1 with 75% of animals surviving despite true prolonged neutropenic and documented bacteremia in 38% of animals. The combination of monoclonal antibodies appears to have an additive effect in providing protection against lethal infection with *Pseudomonas aeruginosa*. The monoclonal antibody treatments did not affect the frequency of bacteremia with *Pseudomonas aeruginosa* yet prevented the lethal effects of Pseudomonas sepsis in these immunocomprised animals.

The combination of antibodies directed against LPS and tumor necrosis factor in addition to standard antimicrobial agents may be the most efficacious therapeutic approach available at this time for use in immunoprophylaxis and therapy of patients at risk from sepsis, for example the febrile neutropenic cancer patient. It seems possible that monoclonal antibody directed against the core glycolipid of LPS would be of value in combination with an anti-TNF mAb in providing the protection against a wide variety of gram negative bacilli in this neutropenic rat model and this is supported by the results presented above at Example 2. Moreover, these results indicate that passive immunotherapy with monoclonal anti-TNF antibody and antiserum against the core glycolipid of gram negative bacteria is beneficial even after the onset of fever and infection in immunocomprised animals.

What is claimed is:

1. A pharmaceutical composition comprising an antibody to tumor necrosis factor (anti-TNF) and an antibody to bacterial lipopolysaccharide (anti-LPS) as a combined preparation for simultaneous mixed, simultaneous separate or sequential use in the therapy of sepsis.

2. The pharmaceutical composition according to claim 1 wherein at least one of the antibody to TNF and the antibody to LPS is a monoclonal antibody.

3. The pharmaceutical composition according to claim 1 in which the anti-LPS antibody recognizes the O-specific side chain of lipopolysaccharide.

4. The pharmaceutical composition according to claim 1 in which the anti-LPS antibody recognizes the core glycolipid of lipopolysaccharide.

5. The pharmaceutical composition according to claim 4 wherein the anti-LPS antibody recognizes the core glycolipid of the lipopolysaccharide of the J5 mutant of *E. coli*.

6. The pharmaceutical composition according to claim 1 further comprising an antimicrobial agent.

7. The pharmaceutical composition according to claim 6 wherein the antimicrobial agent is selected from the group consisting of penicillin, cephalosporin, carbaphem, tetracycline, amyloglycoside, chloramphenicol, erythromycin, vancomycin, amphoterocin and ciprofloxacin.

8. A pharmaceutical composition comprising, in admixture, an anti-TNF antibody and an anti-LPS antibody and a pharmaceutically acceptable excipient, diluent or carrier.

9. The pharmaceutical composition according to claim 8 for the therapy of sepsis.

10. In a process for the production of the pharmaceutical product, the improvement comprising a step of admixing an effective amount of anti-TNF and anti-LPS antibodies.

11. The process according to claim 10, wherein the pharmaceutical product is for the treatment of sepsis associated with Gram negative infection.

12. The process according to claim 10, wherein the pharmaceutical product is for the therapy of neutropenic patients.

13. A method for the treatment of sepsis in a human or animal subject, the method comprising administering to said subject an effective amount of the combination of an anti-TNF antibody in conjunction with an anti-LPS antibody.

* * * * *